(12) United States Patent
Murphy et al.

(10) Patent No.: US 7,229,457 B2
(45) Date of Patent: Jun. 12, 2007

(54) SURGICAL INSTRUMENT WITH ADJUSTABLE ROTARY CUTTING TOOL AND METHOD OF CUTTING

(75) Inventors: John M. Murphy, Haltom City, TX (US); Bryan D. Simmons, Flower Mound, TX (US)

(73) Assignee: Medtronic, Inc., Minneapolis, MN (US)

( * ) Notice: Subject to any disclaimer, the term of this patent is extended or adjusted under 35 U.S.C. 154(b) by 523 days.

(21) Appl. No.: 10/699,471

(22) Filed: Oct. 31, 2003

(65) Prior Publication Data

US 2005/0096685 A1    May 5, 2005

(51) Int. Cl.
*A61B 17/56* (2006.01)
*A61B 17/00* (2006.01)
*A61B 17/32* (2006.01)
*A61B 17/14* (2006.01)
*A61F 5/04* (2006.01)

(52) U.S. Cl. ........................ 606/180; 606/80
(58) Field of Classification Search ................ 606/80, 606/79, 180, 191; 408/153; 407/37, 39
See application file for complete search history.

(56) References Cited

U.S. PATENT DOCUMENTS

| 2,091,628 | A | * | 8/1937 | Carlson ...................... 408/155 |
| 4,047,829 | A | | 9/1977 | Benjamin et al. |
| 4,050,840 | A | | 9/1977 | Skingle |
| 5,122,134 | A | | 6/1992 | Borzone et al. |
| 5,190,548 | A | | 3/1993 | Davis |
| 6,238,398 | B1 | | 5/2001 | Lechot |

OTHER PUBLICATIONS

Linvatec, Power Pro, Attachments [http://www.linvatec.com/products-powerproAtt1.html], retrieved on Oct. 16, 2003.

* cited by examiner

*Primary Examiner*—Anhtuan T. Nguyen
*Assistant Examiner*—Timothy J. Neal
(74) *Attorney, Agent, or Firm*—Haynes and Boone, LLP

(57) ABSTRACT

A surgical cutting tool in which at least one slot is formed through the wall of a tubular housing and receives a blade. An actuator is disposed in the bore and engages the blade so that axial movement of the actuator in the bore causes radial movement of the blade relative to the slot to change the amount of tissue to be removed.

8 Claims, 4 Drawing Sheets

SURGICAL INSTRUMENT WITH ADJUSTABLE ROTARY CUTTING TOOL AND METHOD OF CUTTING

BACKGROUND

This disclosure relates to a surgical instrument with an adjustable rotary cutting tool and to a method of cutting using the tool.

During surgery, rotary cutting tools, such as reamers, are often used to shape and/or enlarge holes or openings in various tissues, including bone. The tools are usually connected by a chuck, collet, or the like, to an electric drive unit that applies relatively high-speed torque to the tool. However, when multiple holes of varying diameters have to be reamed in the same patient, it is necessary to replace each tool with a tool of the proper size.

This problem is especially acute in connection with medical procedures, such as hip and knee replacements, in which canals, or sockets, are prepared in bones to receive implants. It can be appreciated that the canals must be formed with high precision and in as short a time as possible. However, after one canal is formed with a particular tool, the surgeon must remove the tool, select the proper size tool for a new canal and secure the selected tool in the collet, which is tedious and time consuming.

Therefore, what is needed is a single tool that can cut different size bores without having to be replaced.

SUMMARY OF THE INVENTION

One aspect of the present invention provides a surgical cutting tool having a radially adjustable cutting element for use in forming bores of different diameters in tissue of any kind, including bone. In one illustrated aspect, the cutting tool includes a housing having a bore and at least one slot formed through its wall. A cutting element extends through the slot so it may engage tissue for removal. An actuator is provided to adjust the amount of the cutting element that extends beyond the housing. In one aspect, the actuator resides in the bore and is movable therein to adjust the amount of the cutting element that extends beyond the housing. Still further, the actuator may be axially movable within the bore to adjust the cutting element extension.

In still a further aspect of the present invention, there is provided a method of using a surgical cutting instrument having a radially adjustable cutting element. In a preferred aspect, the surgical method comprises extending at least one cutting blade through a slot formed in a tubular housing to adjust the cutting depth. In a more preferred aspect, the extending includes moving an actuator member axially in the housing so that engaging surfaces on the blade causes corresponding radial movement of the blade relative to the slot to adjust the amount of cutting.

In yet a further aspect of the invention, there is provided a surgical cutting tool having a housing having a bore and at least one slot formed through its wall. Preferably, a cutting blade extends through the slot and the housing includes an adjustment mechanism for moving the blade radially relative to the slot to change the amount of cutting.

Certain embodiments may have one or more of the following advantages, however, it should be understood that the advantages, detailed description and specific examples, while indicating features of illustrated embodiments, are intended for the purpose of illustration only and are not intended to limit the scope of the invention.

One advantage associated with an illustrated embodiment is the ability to adjust the cutting diameter of the cutting element.

A further advantage of the present invention includes the ability to form one or more bores in a patient of different diameters with the same cutting element.

In yet a further advantage, a surgical method may be performed on a patient to form bores having multiple sizes without removing the cutting element from the power source.

Still a further advantage that may be incorporated into embodiments of the present invention, is the ability to easily adjust the cutting blade radial depth. Preferably, such an instrument will include a manually actuated adjustment member.

Additional advantages and features of the present invention will become apparent from the following description and appended claims, taken in conjunction with the accompanying drawings.

DETAILED DESCRIPTION

Figure 1:
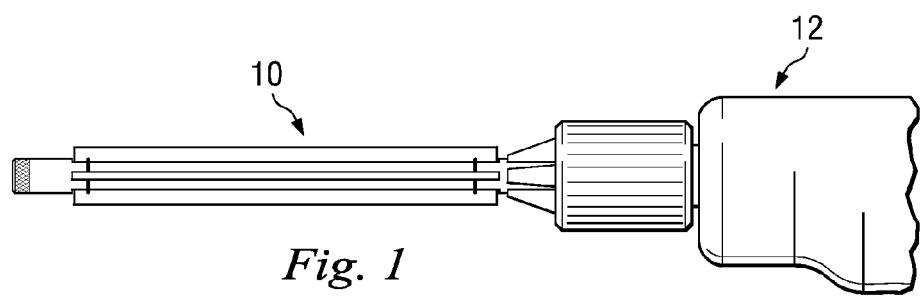
FIG. 1 is a partial elevational view of a surgical reamer according to an embodiment of the invention shown mounted in a driving tool.

Referring to FIG. 1, a reamer is referred to, in general, by the reference numeral 10 and is shown mounted in a conventional collet, or chuck, of an electrical or pneumatic drive unit 12. When actuated, the drive unit 12 applies a relatively high-speed torque to the reamer 10, so that the reamer can be used to cut, shape and/or enlarge holes or openings. An example of the latter would be in medical procedures, such as cranial or orthopedic surgery, in which canals, or sockets, are shaped or enlarged in bones.

Figure 2:
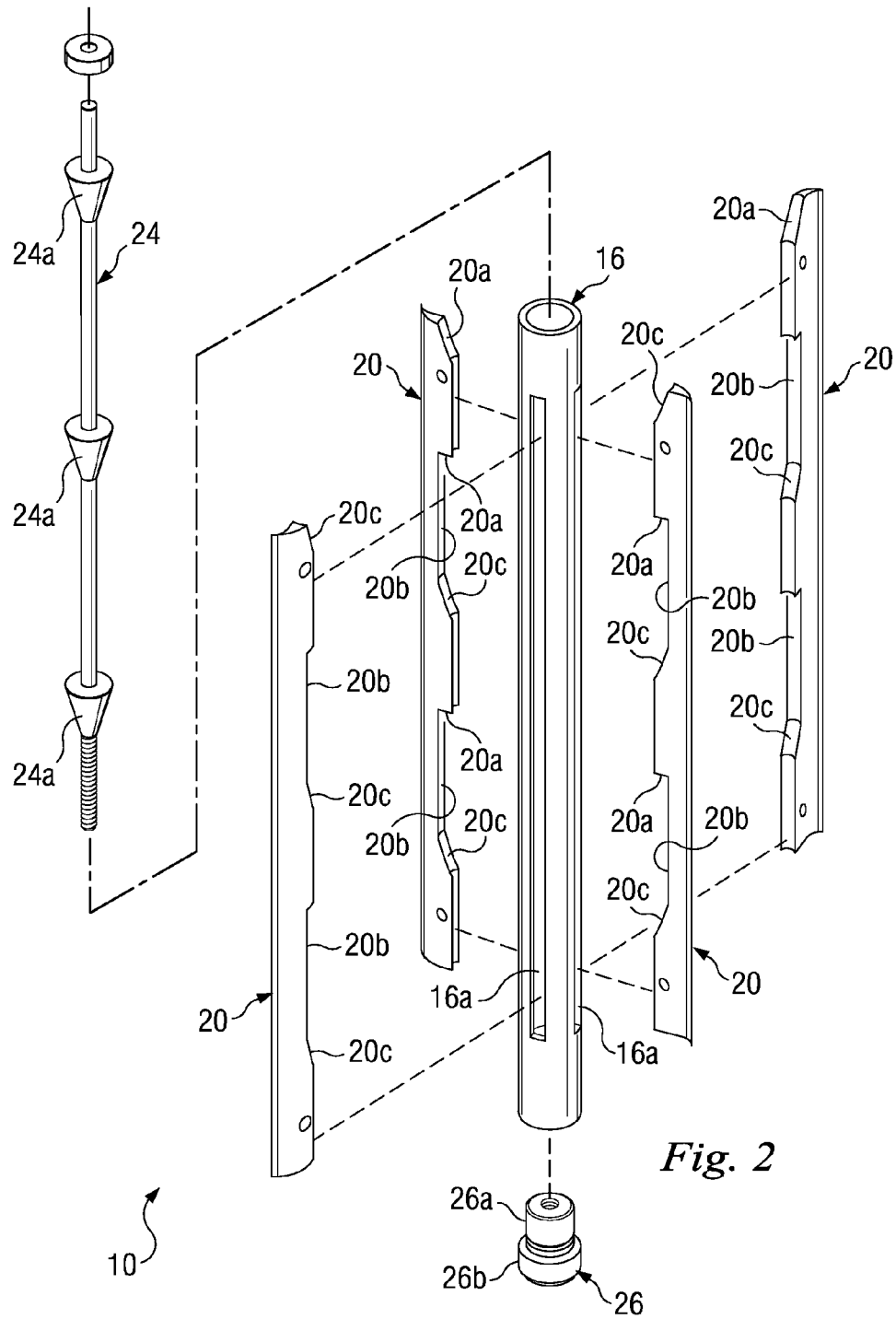
FIG. 2 is an exploded view of the reamer of FIG. 1.

Referring to FIG. 2, the reamer 10 consists of a tubular housing 16 defining a through bore and having four angularly-spaced, radially-extending, slots 16a formed through its wall.

Four cutting blades 20 are provided for extending in the respective slots 16a of the housing 16 in a manner to be described. To this end, the width and length of each blade 20 is slightly less than the width and length of each slot so that the blades fit in the slots with minimal clearance. The outer side surface of each blade 20 is continuous and the inner side surface has two stepped portions 20a, a straight portion 20b extending from each stepped portion, and a tapered surface 20c extending from each stepped portion. The transverse cross-section of each blade 20 is beveled to form a cutting edge that cuts into material in a conventional manner when the blades are rotated about the axis of the housing 16 by the drive unit 12.

The reamer 10 also includes an actuator rod 24 that has three axially-spaced, enlarged, conical surfaces 24a formed thereon. One end of the rod 24 is externally threaded, for reasons to be described. An internally threaded adjustment bolt 26 is also provided that has an internally threaded shank 26a extending from a head 26b.

Figure 3:
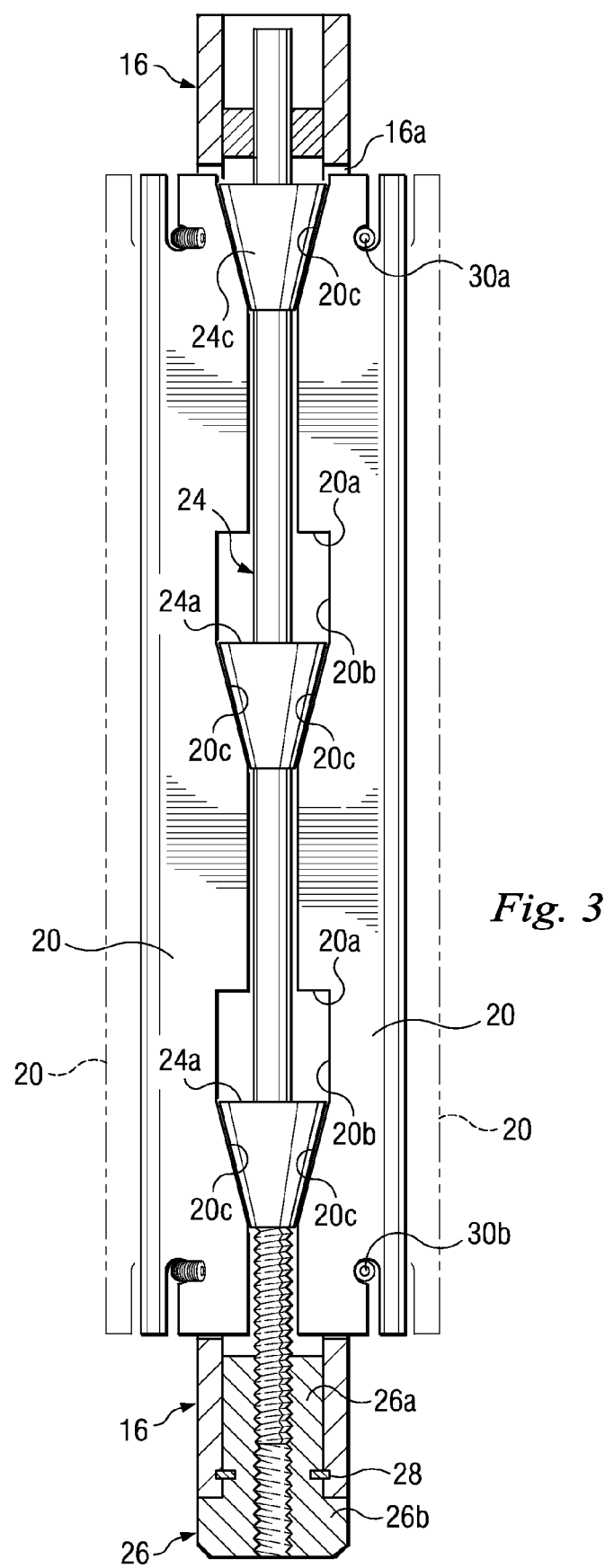
FIG. 3 is a sectional view of the assembled reamer of FIG. 2.

The blades 20, the rod 24, and the bolt 26 are shown assembled in the housing 16 in FIG. 3. In this position, the rod 24 is disposed in the bore of the housing 16, and the shank 26a of the bolt 26 extends through an end of the housing 16 and into the latter bore where it threadedly engages the threaded end portion of the rod 24. The head 26b of the bolt 26 abuts the latter end of the housing 16 so that it can be manually rotated. A snap ring 28 extends in a groove formed in the outer surface of the shank 26a and engages the corresponding wall portion of the housing to help align and secure the shank 26a in the housing 16.

A portion of each blade 20, including the tapered surfaces 20c, extends through a corresponding slot 16a of the housing 16 and into the bore of the housing. The remaining portion of each blade projects radially outwardly from its corresponding slot 16a. As stated above, the width and length of each blade is slightly less than the width and length of each slot, and these dimensions are such to establish a minimal clearance between each blade 20 and its corresponding slot 16a sufficient to permit the blades to move in and out of the slots in a manner to be described.

The spacing between the adjacent conical surfaces 24a of the rod 24 is equal to the spacing between the tapered surfaces 20c of each blade 20, so that each conical surface 24a engages the corresponding tapered surfaces 20c of all four blades.

Two axially spaced springs 30a and 30b are provided near the respective ends of the blades 20, and extend through corresponding notches formed in the blades. The springs 30 are in the form of helical extension garter springs that exert a inwardly-directed radial, or contracting, force in a conventional manner to normally urge the blades 20 radially inwardly so that the tapered surfaces 20c of the blades are urged against the corresponding tapered surfaces 24a of the rods 24.

The blades 20 are shown in their radial innermost position in FIG. 3 as a result of the inward force established by the springs 30. In this position, the outer cutting edges of the blades 20 extend radially outwardly from the outer surface of the housing 16 a predetermined amount to establish a cutting pattern having a circular cross section having a set minimum cutting diameter.

Figure 4A:
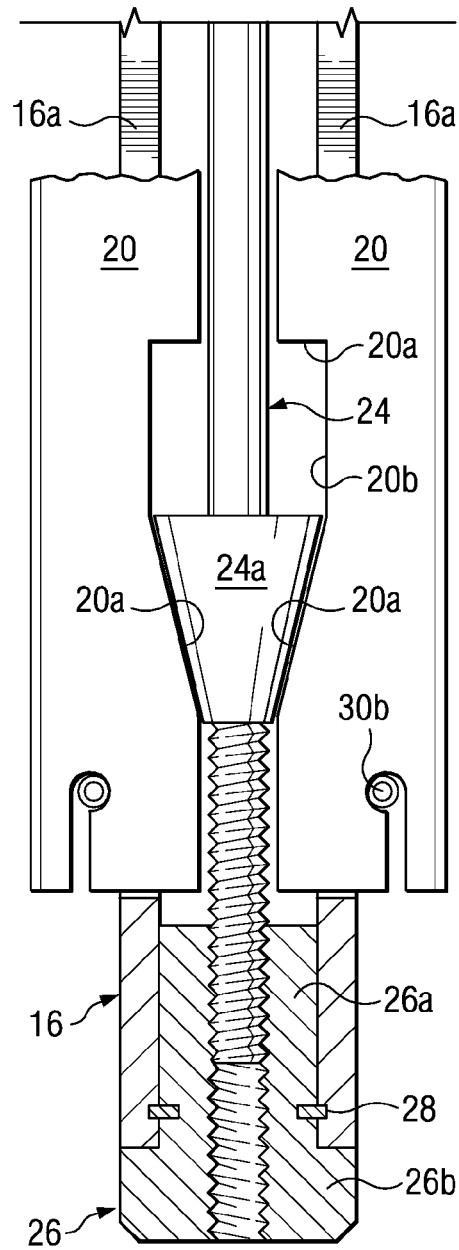
FIGS. 4A and 4B are enlarged partial sectional views of the assembled reamer of FIG. 3 showing two operational modes.
Figure 4B:
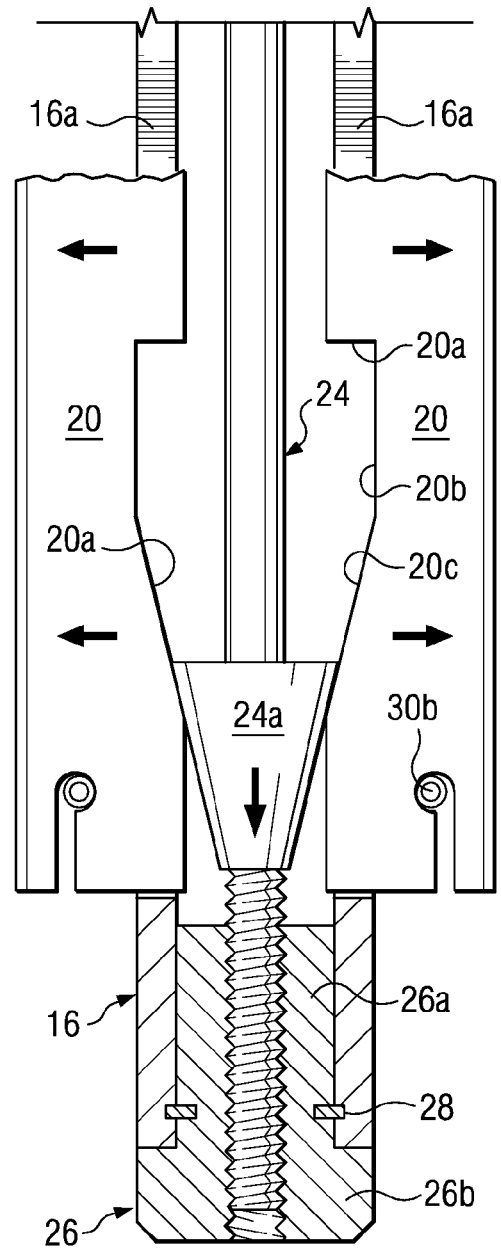

Referring to FIG. 4A, if it is desired to adjust the blades 20 to increase the cutting diameter, the head 26b of the adjustment bolt 26 is manually rotated so as to cause the adjustment rod 24 to move downwardly as viewed in FIG. 4A until it reaches the position of FIG. 4B. In this position the corresponding movement of the conical surfaces 24a (one of which is shown in FIGS. 4A and 4B) exerts a cam force against the corresponding four tapered surfaces 20c of the blades 20 (two of which are shown) to cause the blades to move radially outwardly from the position of FIG. 4A to the position of FIG. 4B. As a result, a larger cutting diameter is established. In the event it is desired to further change the cutting diameter, the head 26b of the adjustment bolt 26 is manually rotated in a manner to cause the adjustment rod 24, and therefore the blades 20, to move accordingly. It is understood that detents, indicia, or other conventional techniques can be utilized to enable the user to adjust the cutting diameter to one of a plurality of predetermined specific values.

Figure 5:
FIG. 5 is an illustration of a surgical reamer in use on a human patient.

Referring now to FIG. 5, there is shown a human patient A prepared for cranial surgery. As set forth above, the reamer 10 and the drive unit 12 permit more than one opening of different diameters to be formed or enlarged in the patient's head without replacing the cutting element. Thus, a surgeon may form a first bore with a first diameter, adjust the cutting element diameter and form a second bore with a second diameter different than the first diameter. While an illustration for cranial surgery is shown, the invention may have application in any patient, human or other animal, through the anatomy. Without limiting the use of the present invention, it may find particular applications in orthopedic surgery including hips, knees, spine, dental, and joints replacements.

Variations and Alternatives

Variations may be made in the foregoing without departing from the scope of the invention and the following are examples:

1. Although the blades 20 are shown and described as being provided with tapered surfaces and the actuator rod 24 with conical surfaces, it is understood that the engaging surfaces of the blades and the rod are not limited to these designs, but rather can vary as long as axial movement of the actuator member causes the radial movement of the blades.
2. The number of surfaces 20a, 20b, 20c and 24a provided on the blades and/or the actuator rod, respectively, can be varied.
3. The number of slots 16a, blades 20 and springs 30 can be varied.
4. The springs 30 can be replaced by any resilient or elastic device for biasing the blades radially inwardly in the manner discussed above.
5. The head 26b of the adjustment bolt can be eliminated and the corresponding end of the shank 26a could be provided with a hexagonal socket, or the like so that it may be turned with a conventional wrench.
7. Spatial references such as "outer", "inner", "radial", "axial", "upwardly", "downwardly", "outwardly", "inwardly", etc., used above are for the purpose of illustration only and do not limit the specific orientation or location of the components described above.
8. The reamer 10 described above can be used for applications other than cranial or orthopedic surgery.
9. Although the cutting tool described above was in the form of a reamer, it is understood that other cutting tools can fall within the scope of the invention.

Although only one exemplary embodiment has been described in detail above, those skilled in the art will readily appreciate that many other variations and modifications are possible in the exemplary embodiment without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A surgical cutting tool comprising:
   a tubular housing having a bore and at least one slot formed through its wall;
   a cutting blade adapted to move relative to the slot and having an inner portion extending in each slot and an outer portion projecting from the slot;
   the outer portion of each blade having a continuous cutting edge;
   the inner edge of each blade having a plurality of spaced straight portions, a series of spaced stepped portions each extending between two straight portions, and a series of tapered surfaces respectively extending from the stepped portions;
   an actuator rod disposed in the bore and having a plurality of spaced straight portions and a plurality of spaced conical surfaces each extending between two straight portions; and
   the straight portions of the blade being aligned with the respective straight portions of the rod, and the tapered surfaces of the blade engaging the respective conical surfaces of the rod so that axial movement of the actuator rod in the bore causes radial movement of each blade relative to its respective slot to vary the size of the cut.

2. The tool of claim 1 wherein one conical surface on the actuator engages a corresponding surface on all of the blades.

3. The tool of claim 1 wherein there is a plurality of angularly spaced slots formed through the housing and a corresponding number of blades respectively mounted in the slots.

4. The tool of claim 3 wherein the blades cut an opening having a circular cross-section and wherein the radial movement of the blades varies the diameter of the cut.

5. The tool of claim 1 further comprising a biasing member for biasing each blade radially inwardly relative to the housing.

6. The tool of claim 5 wherein the biasing member is a garter spring.

7. The tool of claim 1 further comprising an adjustment member engaging the actuator and adapted to be manually actuated for causing the axial movement of the actuator.

8. The tool of claim 7 where in the adjustment member is in threaded engagement with the actuator.

* * * * *